United States Patent
Rappoport et al.

(10) Patent No.: US 7,449,681 B1
(45) Date of Patent: Nov. 11, 2008

(54) MULTI-MODAL IMAGING REGISTRATION CALIBRATION DEVICE AND METHOD

(75) Inventors: Vitaliy Rappoport, Knoxville, TN (US);
Charles Hayden, Knoxville, TN (US);
Robert Smith Stoughton, Oak Ridge, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/744,375

(22) Filed: May 4, 2007

(51) Int. Cl.
*G12B 13/00* (2006.01)

(52) U.S. Cl. .................................. 250/252.1
(58) Field of Classification Search ............. 250/252.1; 378/120
See application file for complete search history.

(56) References Cited

U.S. PATENT DOCUMENTS 4,771,177 A * 9/1988 Brown .................. 250/363.09

2006/0214097 A1 * 9/2006 Wang et al. .............. 250/252.1

OTHER PUBLICATIONS

D. Beque et al., "Optimization of pinhole SPECT calibration", 2003 IEEE Nuclear Symposium Conference Record, 2343-2347.*

* cited by examiner

*Primary Examiner*—David P Porta
*Assistant Examiner*—Kiho Kim
(74) *Attorney, Agent, or Firm*—Peter L. Kendall

(57) ABSTRACT

A phantom and associated method for calibrating registration in a multi-modal medical diagnostic imaging system are presented. The phantom features a plurality of emission point sources arranged in multiple parallel planes along the length of the phantom, with enough planes to allow mode registration to be calibrated over the length of an entire full-body scan. According to the method, calibration scans are performed at each of several scan positions along the length of the phantom, with at least two planes of emission point sources covered by the scan at each position.

17 Claims, 4 Drawing Sheets

MULTI-MODAL IMAGING REGISTRATION CALIBRATION DEVICE AND METHOD

FIELD OF THE INVENTION

In general, the invention relates to multi-modal medical diagnostic imaging. More particularly, the invention relates to a device and method used to calibrate registration between the different imaging modes of a multi-modal imaging system.

BACKGROUND OF THE INVENTION

Diagnostic imaging systems which use multiple imaging modalities are known in the art. For example, it is known to combine CT and PET sub-systems in a multi-modal imaging system to obtain synergistic advantages above and beyond the imaging advantages provided by each type of imagining modality individually. With such a multi-modal system, one imaging modality provides one type of information—for example, the CT modality can provide structural or anatomical patient data—while the other imaging modality provides another type of information—for example, the PET modality provides functional (e.g., blood flow) patient data. Additionally, data from an initial or preliminary CT scan of a patient can be used to generate an attenuation map, which is used to compensate for bodily attenuation of the emissions registered by the PET imaging system.

In order to optimize the benefit of such dual imaging modalities, the images from the two different modes are fused together so that the treating physician can see more clearly and accurately the relationship between the different types of information (i.e., structural and functional). Because the different imaging systems are mounted on different support structures (gantries) and are located at different positions in space with respect to each other, it is necessary to generate a transformation function which brines the separate images into registration with each other and compensates for the difference in vantage points from which the different images are acquired. Such a transformation function is also required in order to relate attenuation data taken from one perspective to attenuation that would be experienced from another perspective. Generating such a transformation function requires that a calibration scan be conducted using a phantom with known geometries and geometric relationship to the patient bed and scanning apparatus.

One arrangement that has been used in the past for such calibration scans has been a pair of short rods installed on the patient bed, with the rods intersecting in three-dimensional space. While such an arrangement has worked well for calibrating a single-position scan, it has not worked so well for multiple-position scans, and errors of as much as 2.5 millimeters in image registration have been measured. It is believed that such errors arise because the precise motion of the patient bed is not perfectly known or predictable over the entire scan range, which results in misalignment between the bed, PET, and CT positions for anything more than a one- or two-position scan. Thus, such a two-rod phantom arrangement is not ideally suited for calibrating a multiple-position scan such as a whole-body scan, which may require as much as five to seven scan positions.

SUMMARY

A calibration device ("phantom") and associated method according to an embodiment of the invention overcomes the deficiencies of such prior art calibration devices. In a first aspect, the invention features a scan registration calibration device (phantom). The phantom includes a support member and a multiplicity of emission point sources supported by the support member. The emission point sources are disposed within a plurality of parallel planes distributed along a length of the support member.

In exemplary embodiments, three emission point sources may be arranged in a triangular configuration to define each of the planes, and the triangular configuration may invert on successive planes. Suitably, fourteen of such planes are each spaced apart by about 68 millimeters over the entire 90 centimeter length of the phantom. The support member is suitably made from STYROFOAM, with the emission point sources embedded therein. The emission point sources may be made from germanium and titanium and sized to emit approximately 2 µCi of radiation.

In another embodiment, the invention features a method for calibrating registration between a pair of imaging modalities in a multi-modal medical diagnostic imaging system. According to the method, a phantom is placed on the patient pallet of the imaging system. The phantom has a multiplicity of emission point sources disposed within a plurality of parallel planes distributed along a lengthwise direction of the phantom, and the phantom is placed on the patient pallet such that the lengthwise direction of the phantom is aligned with a lengthwise direction of the patient pallet. The phantom is then scanned using both of the imaging modalities at each of a plurality of scanning positions to generate first and second sets of imaging data corresponding to the pair of imaging modalities, with at least two of the planes being contained within the field of view of at least one of the imaging modalities at each of the scanning positions. The phantom is scanned at enough scanning positions such that all of the emission point sources are scanned. The first and second sets of imaging data are processed to generate a registration transfer function by means of which scan data obtained from the vantage point of one of the pair of imaging modalities can be mapped to the vantage point of the other of the pair of imaging modalities.

In exemplary embodiments of the method, three of the planes may be contained within the field of view of the at least one imaging modality at each of the scanning positions, and the phantom may be scanned at a plurality of locations. Preferably, the field of view of the at least one imaging modality at each of the scanning locations overlaps with the field of view of the imaging modality at another of the scanning locations.

BRIEF DESCRIPTION OF THE DRAWINGS

Exemplary embodiments of the invention will now be described in greater detail in connection with the drawings, in which.

DETAILED DESCRIPTION OF EMBODIMENTS OF THE INVENTION

Phantom

Figure 1:
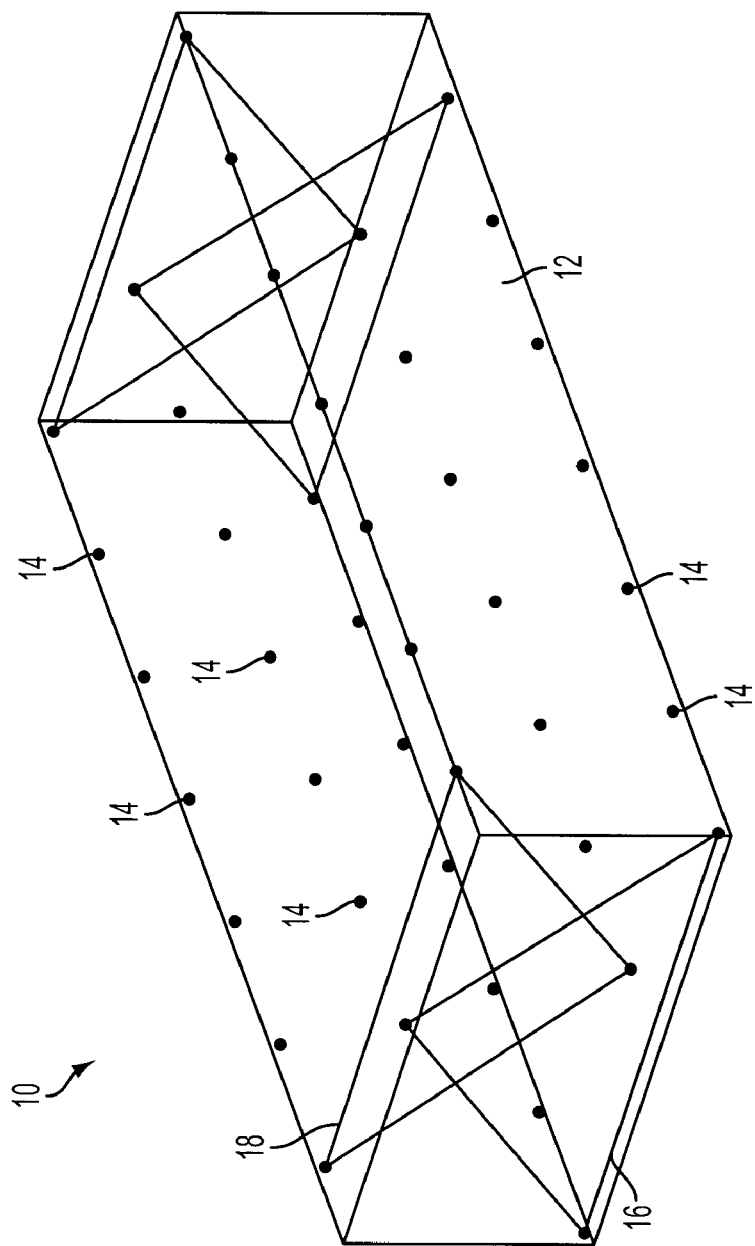
FIG. 1 is a perspective view of a calibration phantom according to an embodiment of the invention.

A scan calibration device (phantom) 10 according to the invention is illustrated in FIGS. 1 through 4. The phantom 10 includes a support member 12 and a multiplicity of emission point sources 14 embedded in and distributed across the support member in a highly precise arrangement, which is described below.

The support member 12 is a generally rectilinear, brick-shaped member that is long enough to provide calibration for an entire body scan. For current scanning systems, 90 centimeters is sufficient length. Although a perfectly square cross-section (taken transverse to the lengthwise axis of the support member) might be ideal, the phantom 10 must fit on top of the pallet of the patient handling system. Therefore, a rectangular cross-section allows for maximum spreading of the point sources on top of the pallet while still allowing the phantom 10 to fit within the tunnel of the scanning system gantry. For current scanning systems, a width of 16 inches (40.64 centimeters) and a height of 8 inches (20.32 centimeters) is sufficient.

It should be appreciated by those skilled in the art that a length of 90 centimeters is exemplary. Other lengths, weights and widths can be used and still fall within the scope of the invention.

The support member 12 may be fabricated from any material that is radio-transparent and that allows the emission point sources 14 to be embedded in it fairly easily. Polystyrene foam, more commonly known as STYROFOAM, is one such material that may be used.

The emission point sources 14 preferably are made from germanium, with titanium powder added to provide better visualization in the CT scan. Each point source is 2 millimeters in diameter and 2 millimeters long, which provides a radiation emission level of about 2 µCi.

Figure 4:
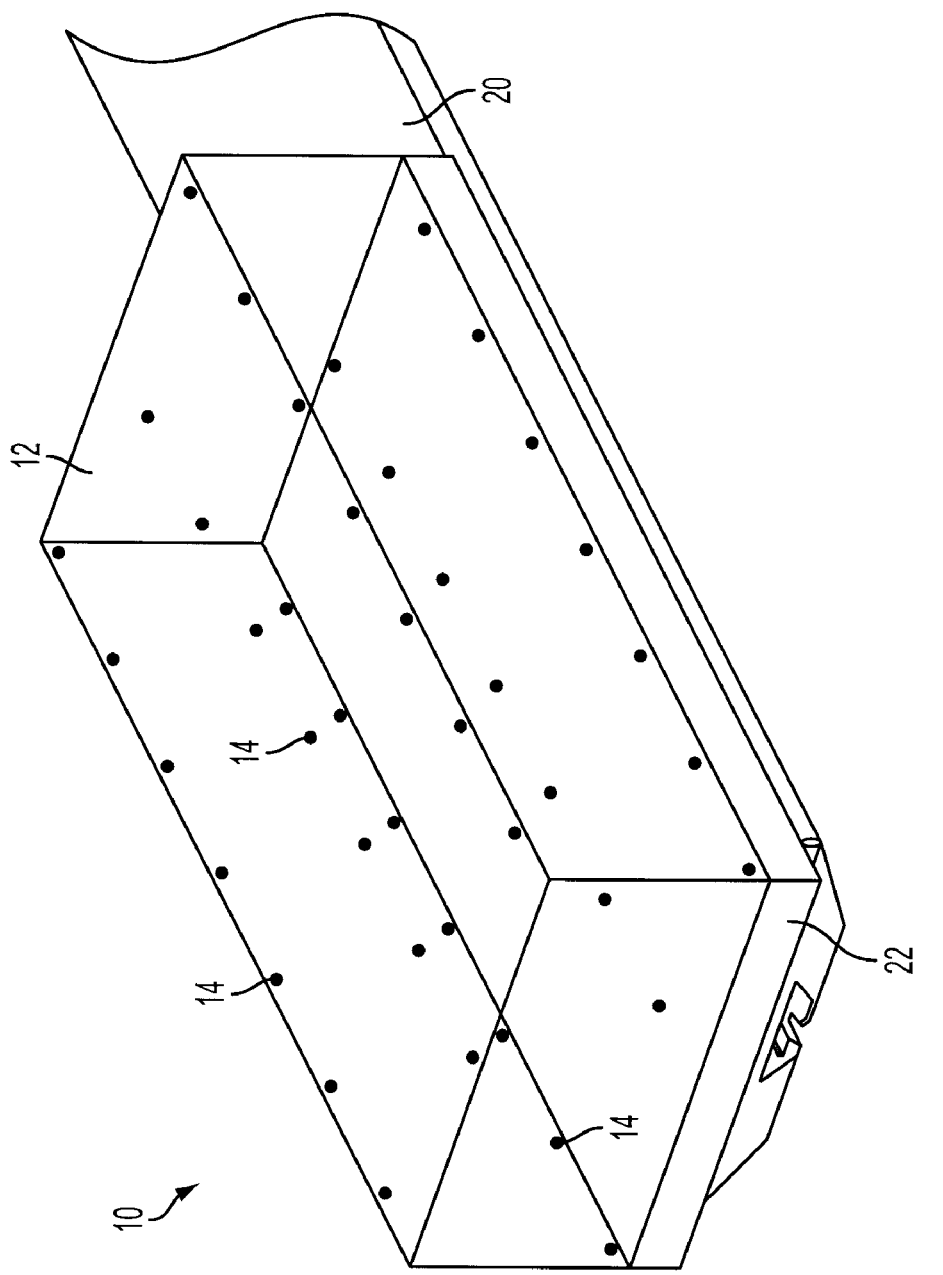
FIG. 4 is a perspective view illustrating a calibration set-up using the phantom shown in FIG. 1.

As best illustrated in FIGS. 1 and 4, the emission point sources 14 are arranged in a plurality of parallel planes along the length of the support member 12, with the longitudinal axis of the support member 12 being normal to each plane. For example, in the illustrated embodiment, three emission point sources arranged in a triangular pattern define each plane, and the planes are spaced apart by 68 millimeters. Other geometric arrangements of emission point sources which all lie within a common plane are, of course, deemed to be within the scope of the present invention.

Furthermore, in the illustrated embodiment, the plane-defining geometric arrangement of emission point sources 14 is "inverted" on each successive plane. Thus, on one plane (e.g., the leftmost plane 16 in FIG. 1), two emission point sources 14 are located near the bottom longitudinal edges of the support member 12 (i.e., where the side surfaces of the support member join the bottom surface) and a third emission point source is centrally located (i.e., half way between the side surfaces) at the top surface of the support member 12; on the next adjacent plane (e.g., the plane 18 in FIG. 1), on the other hand, two emission point sources 14 are located near the top longitudinal edges of the support member 12 (i.e., where the side surfaces of the support member join the top surface) and a third emission point source is centrally located at the bottom surface of the support member 12. (The triangles (and hence planes) defined by the six emission point sources 14 at each of the left and right ends of the support member 12 are specifically illustrated; the remainder are omitted for clarity.) In the illustrated embodiment, this arrangement is repeated seven times over the length of the support member 12, for a total of 42 emission point sources (3×2×7).

Figure 2:
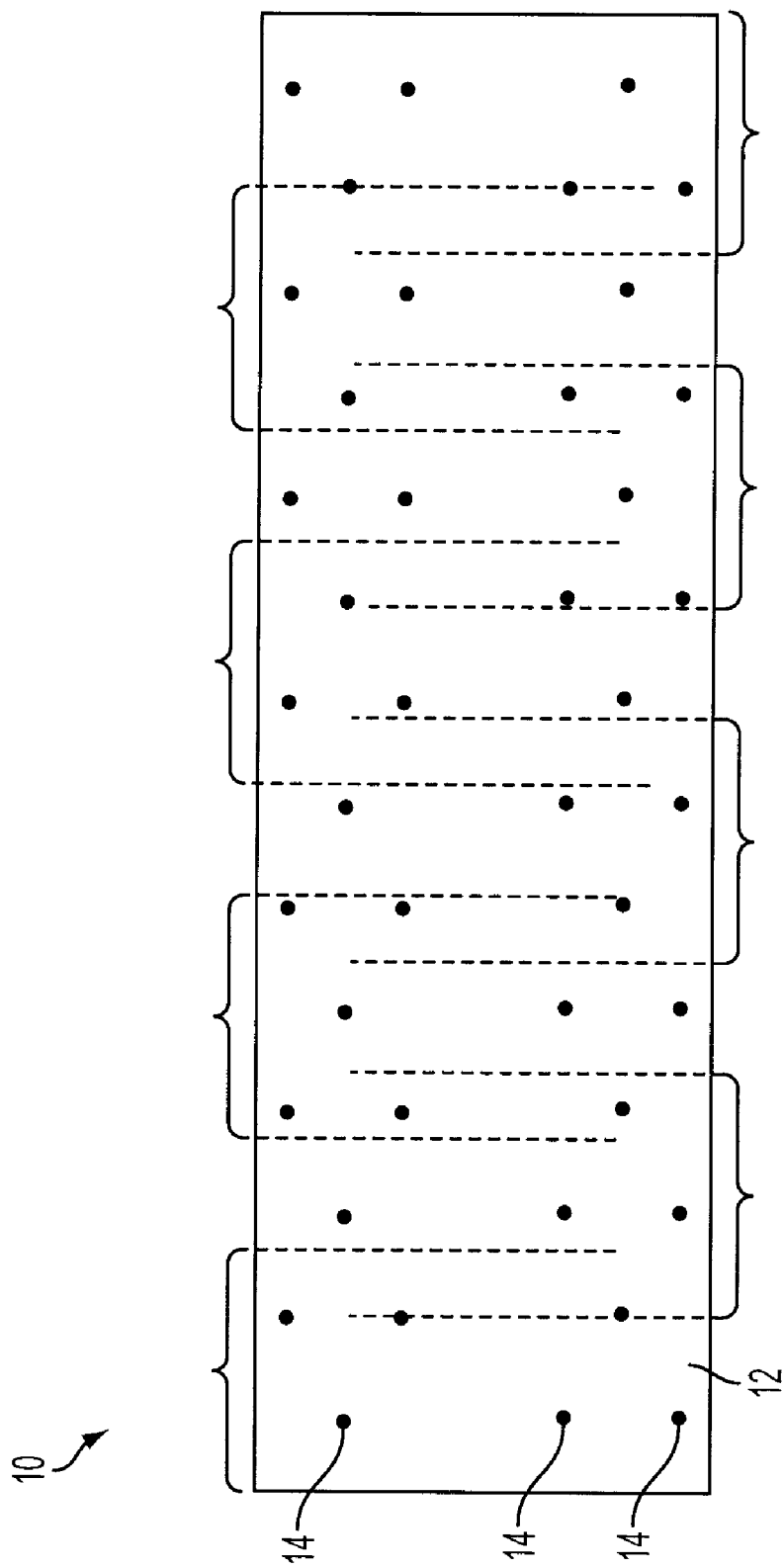
FIG. 2 is a side view, taken at an oblique elevational angle, illustrating emission point sources scanned at each bed position with a standard three-ring PET scanner.
Figure 3:
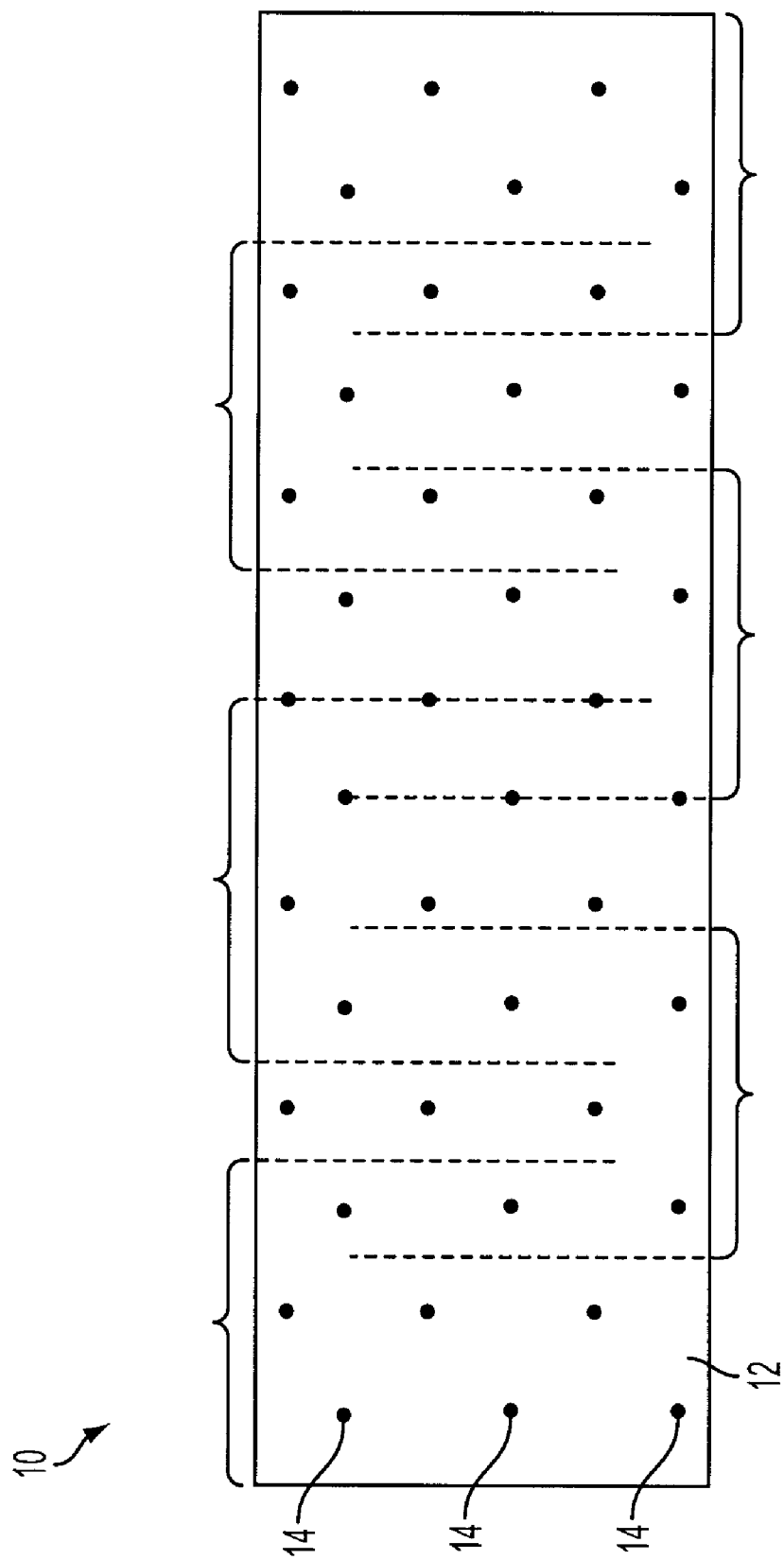
FIG. 3 is a side view, taken at an oblique elevational angle, illustrating emission point sources scanned at each bed position with a standard four-ring PET scanner.

This arrangement of emission point sources in parallel planes, and the longitudinal spacing of the planes, ensures that at least six emission point sources, and possibly nine depending on the type of PET scan apparatus employed, can be scanned for each bed location in a standard PET scanning system, with overlapping PET fields of view for each of the bed locations. For example, a standard three-ring PET scanner has a field of view that is 162 millimeters wide and an associated bed position spacing of 117.5 millimeters, with eight overlapping scan positions along the length of the phantom demarcated by brackets and dashed lines as illustrated in FIG. 2. (In FIGS. 2 and 3, the phantom 10 is depicted as if it is rotated slightly about its longitudinal axis, so that all three plane-defining emission point sources 14 are visible for each defined plane.) Given the above-noted spacing of 68 millimeters between the planes of the emission point sources, two such planes—i.e., six emission point sources—easily fall within the three-ring PET scanner field of view at all scan positions along the length of the phantom. Similarly, a standard four-ring PET scanner has a field of view that is 216 millimeters wide and an associated bed position spacing of 150 millimeters, with six overlapping scan positions along the length of the phantom demarcated by brackets and dashed lines as illustrated in FIG. 2. Given the spacing of 68 millimeters between the planes of the emission point sources, three such planes—i.e., nine emission point sources—easily fall with the four-ring PET scanner field of view at all scan positions along the length of the phantom.

Use of Phantom in Registration Calibration

To calibrate registration of a multi-modal imaging system, e.g., a PET/CT imaging system, a phantom 10 according to the invention is preferably supported by about one to two inches (2.54 to 5.08 centimeters) above the pallet 20 of an imaging system, e.g., by another piece of STYROFOAM 22, as illustrated in FIG. 4. This makes it easier to isolate the emission point sources from the pallet 20 in the CT image before processing the image to find the centers of the emission point sources.

A six-position bed scan (in the case of a four-ring PET scanner) is then collected that covers the entire length of the phantom 10 and contains 42 emission point sources that are detected in both PET and CT. Since the system model includes gantry rotation as a parameter, each PET volume must be processed separately. On the other hand, since the CT data is collected as one contiguous volume, it must be repartitioned into six individual volumes that correspond to the PET volumes. There is no method currently in the existing commercially available PET/CT software to process the PET bed positions individually without stitching them together in the end, so this process actually begins with the PET sinograms and performs a simple filtered back-projection reconstruction without attenuation correction. The reconstructions are performed at full resolution, and the Z location of the PET volume is known from the bed position.

Once the PET volumes have been reconstructed and the CT volumes assembled by accumulating slices with matching Z coordinates, the conjugate points can be located. In both the PET and CT scans, the emission point sources will appear as small bright spheres in the volume and can be located relatively easily using a simple thresholding and localization algorithm; the three-dimensional coordinate of the centroid of each extracted sphere is used as the location of the observation. Once these three-dimensional coordinates are found for all emission point sources in both imaging modalities, they must each be converted to spatial coordinates using the parameters specific to each gantry. For example, the definition of the origin in each slice and the pixel size are unique specifications that will allow the transformation of image coordinates in pixels to spatial coordinates in millimeters. Once these conjugate points exist in a spatial coordinate system, they can be compared and fitted to determine how to align the gantries.

A standard photogrammetric process is employed that takes observations from two independent sources and does a least squares fit between the conjugate points using a model of the expected transformation between the points. (In practice, translation as well as rotation between the points is to be expected, from one or both of the gantries being tilted, and a shear is also to be expected, from the bed possibly not coming into the gantries exactly perpendicular to the imaging planes.) This method is known in the art at least via a paper published by Charles Stearns in 2003 and entitled "Measuring Gantry-Gantry and Gantry-Table Alignment in PET/CT," Nuclear Science Symposium Conference Record, 2003, IEEE Vol. 4, October 19-25, pages 2481-2485. Once the model parameters have been determined, the PET point locations can be transformed into the CT coordinate system and residual error can be observed. Using this process, the average residual error has been typically observed in conjugate points at 2 millimeters for just a translation shift and under 0.5 millimeters for a full model including rotation and shear. This registration is applied in the reconstruction of each bed position to make a whole body volume that is best registered between the PET and CT modalities.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

We claim:

1. A phantom for use in calibrating a nuclear medical imaging system, comprising:
    a support member; and
    a multiplicity of emission point sources supported by the support member;
    wherein a plurality of emission point sources are disposed within each of a plurality of parallel planes distributed along a length of said support member in a scanning direction of said imaging system.

2. The phantom of claim 1, wherein a plane is defined by three emission point sources arranged in a triangular configuration.

3. The phantom of claim 2, wherein the triangular configuration inverts on successive planes.

4. The phantom of claim 1, wherein said planes are spaced apart by a preselected distance such that at least two planes are within a field of view of said system for any given scan position.

5. The phantom of claim 1, wherein said phantom is 90 centimeters long.

6. The phantom of claim 1, wherein said phantom is 90 centimeters long and includes fourteen of said planes spaced apart by 68 millimeters.

7. The phantom of claim 1, wherein said support member is made from polystyrene foam and said emission point sources are embedded therein.

8. The phantom of claim 1, wherein said emission point sources comprise germanium and titanium.

9. The phantom of claim 8, wherein said emission point sources are sized to emit approximately 2 µCi.

10. A method for calibrating registration between a pair of imaging modalities in a multi-modal medical diagnostic imaging system having a patient pallet, comprising:
    placing a phantom on the patient pallet, said phantom having a multiplicity of emission point sources disposed within a plurality of parallel planes distributed along a lengthwise direction of the phantom and the phantom being placed on the patient pallet such that the lengthwise direction of the phantom is aligned with a lengthwise direction of the patient pallet;
    scanning the phantom using both of said imaging modalities at each of a plurality of scanning positions to generate first and second sets of imaging data corresponding to said pair of imaging modalities, at least two of said planes being contained within the field of view of at least one of said imaging modalities at each of said scanning positions and said phantom being scanned at enough scanning positions such that all of the emission point sources are scanned; and
    processing said first and second sets of imaging data to generate a registration transfer function by means of which scan data obtained from the vantage point of one of said pair of imaging modalities can be mapped to the vantage point of the other of said pair of imaging modalities 11. The method of claim 10, wherein three of said planes are included within the field of view of said at least one of said imaging modalities at each of said scanning positions.

12. The method of claim 11, wherein said phantom is scanned at least six scanning positions.

13. The method of claim 10, wherein said phantom is scanned at eight scanning positions.

14. The method of claim 10, wherein the field of view of said at least one imaging modality at each of said scanning locations overlaps with the field of view of said at least one imaging modality at another of said scanning locations.

15. The method of claim 10, wherein one of said imaging modalities is Positron Emission Tomography (PET).

16. A phantom for use in calibrating a nuclear medical imaging system, comprising:
    a solid support member; and
    a plurality of emission point sources embedded in said solid support member such that a subset plurality of said plurality of emission point sources defines a plane within said solid support member, a plurality of parallel planes being distributed along a length of said solid support member.

17. The phantom of claim 16, wherein said solid support member is made of polystyrene foam.

* * * * *